US008623060B2

(12) United States Patent
Vlahos et al.

(10) Patent No.: US 8,623,060 B2
(45) Date of Patent: Jan. 7, 2014

(54) CANNULATED BONE SCREW (75) Inventors: Jeff Vlahos, Marquette, MI (US);
Matthew N. Songer, Marquette, MI (US); Kenneth Davenport, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 1588 days.

(21) Appl. No.: 11/691,247

(22) Filed: Mar. 26, 2007

(65) Prior Publication Data
US 2007/0250063 A1 Oct. 25, 2007

Related U.S. Application Data (63) Continuation of application No. 10/365,698, filed on Feb. 12, 2003, now Pat. No. 7,207,994.

(60) Provisional application No. 60/356,221, filed on Feb. 12, 2002.

(51) Int. Cl.
*A61B 17/86* (2006.01)
(52) U.S. Cl.
USPC ........................................ 606/270; 623/22.35
(58) Field of Classification Search
USPC .................... 623/17.11–17.16, 22.35–22.36
See application file for complete search history.

(56) References Cited

U.S. PATENT DOCUMENTS

| 4,175,555 A | 11/1979 | Herbert |
| 5,443,509 A | 8/1995 | Boucher et al. |
| 5,564,302 A * | 10/1996 | Watrous .......................... 72/458 |
| 5,743,914 A | 4/1998 | Skiba |
| 2002/0052605 A1* | 5/2002 | Grooms et al. ................. 606/72 |

FOREIGN PATENT DOCUMENTS

WO PCT/US03/04069 5/2008

OTHER PUBLICATIONS

Brochure, "Magna-Fx® Cannulated Screw Fixation System," Zimmer, Inc., pp. 1-8.
Brochure, Mini Magna-Fx® Cannulated Screw Fixation System, Zimmer, Inc., 1995, 1997, 1998, pp. 1-8.
Brochure, "3.0 mm Cannulated Screw and Threaded Washing," Synthes, Sep. 1998, pp. 1-14.
Brochure, "Biodrive Cannulated Screw—Accurate, Precise, and a Complete System," Biomet Merck Limited, Bridgend, South Wales, Orthopaedic Product News, Nov. 2000, pp. 1, 37.
Brochure, "Cannulated Screw System™," OsteoMed Corporation, 2 pages.
Brochure, "The Large Cannulated Screw System," Synthes , 5 pages.

(Continued)

*Primary Examiner* — David Isabella
*Assistant Examiner* — Ann Schillinger
(74) *Attorney, Agent, or Firm* — Fitch, Even, Tabin & Flannery LLP (57) ABSTRACT

A small cannulated bone screw is provided having an optimized combination of strength, cannula size and thread depth. A set of such strong and small size screws is also provided where the smallest sizes can have one performance ratio emphasized over another, and the larger sizes can have the emphasis reversed. In particular, the smallest screws optimize the combination of their strength and cannula size with the larger screws optimizing the combination of their strength and thread depth. In any event, each of the screws in the set has an optimized combination of strength, cannula size and thread depth throughout the full range of screw sizes in the set, e.g. 3.0 mm to 7.5 mm major diameters.

23 Claims, 6 Drawing Sheets (56) References Cited

OTHER PUBLICATIONS

Brochure, "7.3 mm Cannulated Screw Technique Guide," Synthes, 7 pages.
Brochure, "4.0mm Cannulated Screw Technique Guide," Synthes, Sep. 1995, 7 pages.
Brochure, "The Small Cannulated Screw System," Synthes, Jul. 1989, 6 pages.
Brochure, "ECT® Internal Fracture Fixation System," Zimmer, Inc., 1994, 1996, 1998, 3 pages.
Data Sheet, "Synthes Cannulated Screws, Guide Wires, Drill Bits and Taps," Synthes.
Data Sheet, "Synthes Screws, Drill Bits and Taps," Synthes, Jan. 1997.
Source Unknown, "Stainless Steel Implants," Mar. 1997.
Article, "Synthes Update," Synthes, Aug. 1999.
Article, "New Products," see Cannulated Screw.
Brochure, "Trauma," Smith & Nephew, 1999.
Internet Web Page, "Large Cannulated Screw System," Biomet, downloaded Jul. 22, 1999.
Internet Web Page, "ORTHEX Cannulated Bone Screws," Vilex.
Internet Web Page, "ORTHEX Cannulated Bone Screws," Vilex, downloaded Mar. 30, 1999.
Data Sheet, "Alloy Data, BioDur 316LS Stainless," Carpenter Specialty Alloys, original copyright, 1995; printed, Dec. 1998, 3 pages.
Data Sheet, "BioDur Alloys . . . ," Carpenter Specialty Alloys, printed, Jul. 1998; 2 pages.
Data Sheet, "Alloy Data, BioDur 108 Alloy," Carpenter Specialty Alloys, original copyright 1999; printed, Sep. 1999, 5 pages.
Internet Webpage, "Showstoppers: A selection of innovative new products and services exhibited at MD&M West 99," Advanced Technical Consultants, downloaded Sep. 16, 2005.
An International Search Report dated Aug. 13, 2003, from the International Bureau in corresponding International (PCT) Application No. PCT/US2003/04069.

* cited by examiner

| SCREW SIZE (MM) | P(IN) | F(IN) | R1(IN) | R2(IN) | B(DEG) | A(DEG) | MIN. D. (IN) | MAJ. D. (IN) | CANNULA DIA. (IN) | THREAD DEPTH (IN) | WALL THICKNESS (IN) | TSF | LEAD ANGLE |
|---|---|---|---|---|---|---|---|---|---|---|---|---|---|
| 3.0 | 0.0490 | 0.003 | 0.031 | 0.01 | 25 | 5 | 0.074 | 0.118 | 0.053 | 0.022 | 0.0105 | 0.759 | x.xxxxxxx |
| 3.5 | 0.0490 | 0.003 | 0.031 | 0.01 | 25 | 5 | 0.096 | 0.138 | 0.068 | 0.021 | 0.014 | 0.747 | 7.597095 |
| 4.0 | 0.0690 | 0.003 | 0.04 | 0.015 | 30 | 5 | 0.090 | 0.157 | 0.068 | 0.0335 | 0.011 | 0.780 | 10.08913 |
| 4.5 | 0.0690 | 0.004 | 0.04 | 0.015 | 30 | 5 | 0.125 | 0.177 | 0.098 | 0.026 | 0.0135 | 0.718 | 8.279938 |
| 5.5 | 0.0890 | 0.004 | 0.03 | 0.015 | 20 | 10 | 0.146 | 0.217 | 0.098 | 0.0355 | 0.024 | 0.730 | 8.875905 |
| 6.5 | 0.1060 | 0.006 | 0.047 | 0.03 | 30 | 5 | 0.177 | 0.256 | 0.134 | 0.0395 | 0.0215 | 0.711 | 9.027021 |
| 7.0 | 0.1060 | 0.006 | 0.047 | 0.03 | 30 | 5 | 0.177 | 0.276 | 0.134 | 0.0395 | 0.0215 | 0.711 | 8.63462 |
| 7.5 | 0.1060 | 0.006 | 0.047 | 0.03 | 30 | 5 | 0.186 | 0.295 | 0.134 | 0.0545 | 0.026 | 0.791 | 8.138918 |

PRE ELECTROPOLISH

| SCREW SIZE (MM) | P(IN) | F(IN) | R1(IN) | R2(IN) | B(DEG) | A(DEG) | MIN. D. (IN) | MAJ. D. (IN) | CANNULA DIA. (IN) | THREAD DEPTH (IN) | WALL THICKNESS (IN) | TSF | LEAD ANGLE |
|---|---|---|---|---|---|---|---|---|---|---|---|---|---|
| 3.0 | 0.0490 | 0.003 | 0.031 | 0.01 | 25 | 5 | 0.755 | 0.120 | 0.053 | 0.022 | 0.01125 | 0.762 | 9.07033 |
| 3.5 | 0.0490 | 0.003 | 0.031 | 0.01 | 25 | 5 | 0.0975 | 0.14 | 0.068 | 0.021 | 0.01475 | 0.744 | 7.51771 |
| 4.0 | 0.0690 | 0.003 | 0.04 | 0.015 | 30 | 5 | 0.092 | 0.159 | 0.068 | 0.03375 | 0.01175 | 0.782 | 9.951 |
| 4.5 | 0.0690 | 0.004 | 0.025 | 0.01 | 25 | 10 | 0.1255 | 0.186 | 0.098 | 0.03025 | 0.01375 | 0.753 | 8.03076 |
| 5.5 | 0.0890 | 0.004 | 0.03 | 0.015 | 20 | 10 | 0.1465 | 0.218 | 0.098 | 0.03575 | 0.02425 | 0.732 | 8.83996 |
| 6.5 | 0.1080 | 0.006 | 0.047 | 0.03 | 30 | 5 | 0.1775 | 0.257 | 0.134 | 0.03975 | 0.02175 | 0.712 | 8.99367 |
| 7.0 | 0.1080 | 0.006 | 0.047 | 0.03 | 30 | 5 | 0.1865 | 0.277 | 0.134 | 0.04525 | 0.02625 | 0.742 | 8.44186 |
| 7.5 | 0.1080 | 0.006 | 0.047 | 0.03 | 30 | 5 | 0.1865 | 0.296 | 0.134 | 0.05475 | 0.02625 | 0.793 | 8.11395 |

FINAL

| SCREW SIZE (MM) | P(IN) | F(IN) | R1(IN) | R2(IN) | B(DEG) | A(DEG) | MIN. D. (IN) | MAJ. D. (IN) | CANNULA DIA. (IN) | THREAD DEPTH (IN) | WALL THICKNESS (IN) | TSF | LEAD ANGLE |
|---|---|---|---|---|---|---|---|---|---|---|---|---|---|
| 3.0 | 0.0490 | 0.003 | 0.031 | 0.01 | 25 | 5 | 0.075 | 0.119 | 0.053 | 0.022 | 0.011 | 0.759 | 9.13928 |
| 3.5 | 0.0490 | 0.003 | 0.031 | 0.01 | 25 | 5 | 0.097 | 0.139 | 0.068 | 0.021 | 0.0145 | 0.747 | 7.533455 |
| 4.0 | 0.0690 | 0.003 | 0.04 | 0.015 | 30 | 5 | 0.091 | 0.158 | 0.068 | 0.0335 | 0.0115 | 0.780 | 10.00974 |
| 4.5 | 0.0690 | 0.004 | 0.025 | 0.01 | 25 | 10 | 0.125 | 0.185 | 0.098 | 0.03 | 0.0135 | 0.751 | 8.069113 |
| 5.5 | 0.0890 | 0.004 | 0.03 | 0.015 | 20 | 10 | 0.146 | 0.217 | 0.098 | 0.0355 | 0.024 | 0.730 | 8.875905 |
| 6.5 | 0.1080 | 0.006 | 0.047 | 0.03 | 30 | 5 | 0.177 | 0.256 | 0.134 | 0.0395 | 0.0215 | 0.711 | 9.027021 |
| 7.0 | 0.1080 | 0.006 | 0.047 | 0.03 | 30 | 5 | 0.186 | 0.276 | 0.134 | 0.045 | 0.026 | 0.741 | 8.468876 |
| 7.5 | 0.1080 | 0.006 | 0.047 | 0.03 | 30 | 5 | 0.186 | 0.295 | 0.134 | 0.0545 | 0.026 | 0.791 | 8.138918 |

FIG. 6

| MAJOR DIA. | COMPETITOR CANNULA DIA. | COMPETITOR GUIDE PIN DIA. | PST CANNULA DIA. (MM) | MAX PST GUIDE PIN DIA. GUIDE PIN DIA. (MM) |
|---|---|---|---|---|
| 7.5 | NA | 3.2 | 3.40 | 3.3 |
| 7.0 | 2.11 TO 3.30 | 1.8 TO 3.2 | 3.40 | 3.3 |
| 6.5 | 2.49 | 2.0 TO 3.2 | 3.40 | 3.3 |
| 5.5 | 2.11 | 1.9 | 2.49 | 2.39 |
| 4.5 | 1.75 | 1.0 TO 2.0 | 2.49 | 2.39 |
| 4.0 | 1.37 TO 1.70 | 1.0 TO 2.0 | 1.73 | 1.63 |
| 3.5 | 1.37 | 1.25 TO 1.6 | 1.73 | 1.63 |
| 3.0 | 1.24 | 1.1 | 1.35 | 1.25 |

| MAJOR DIA | MAX BENDING MOMENT COMP | MAX BENDING MOMENT PST | MAX SHEAR BENDING MOMENT COMP | MAX SHEAR BENDING MOMENT PST |
|---|---|---|---|---|
| 7.5 | | 92.33601 | | 92.3125 |
| 7.0 | 66.155 TO 92.194 | 60.0711 TO 92.3360 | 66.138 - 92.171 | 60.0558 TO 92.3125 |
| 6.5 | 68.421 | 62.8397 TO 73.1327 | 68.404 | 62.8237 TO 92.3125 |
| 5.5 | 45.544 | 48.7146 | 45.532 | 48.7022 |
| 4.5 | 12.934 | 23.8671 TO 32.2395 | 12.931 | 23.861 TO 32.2313 |
| 4.0 | 8.427 TO 17.126 | 10.1855 | 8.425 TO 17.122 | 10.1829 |
| 3.5 | 10.907 | 13.0019 | 10.904 | 12.9986 |
| 3.0 | 4.635 | 5.8644 | 4.634 | 5.8629 |

FIG. 7

CANNULATED BONE SCREW

FIELD OF THE INVENTION

The invention relates to bone screws and, more particularly, to small bone screws that are cannulated.

BACKGROUND OF THE INVENTION

Cannulated bone screws provided with an axial throughbore or cannula extending therethrough are known to allow use of guide wires that penetrate a bone at the desired implant site for the screw and guide the screw as it is being rotatably driven into the bone. One well known problem with bone screws is that as they start to go down in size in terms of the outer diameter of their threads, i.e., major diameter, the cannulas thereof likewise become very small so that only very thin guide wires can be used therewith. These thin guide wires are fairly flimsy and thus tend to bend and buckle, and walk on the surface of the bone when being inserted into the bone material. When this occurs, the location and/or angle of penetration varies from that which is desired making for inaccuracies in implanting the screw. In some instances, the screw will need to be backed out ruining the site and requiring identification of another implantation site, which can be difficult depending on the bone and bone location, and in any event is inconvenient to the doctor applying the screw into the bone.

Strength characteristics, such as the bending and torsional strength of a screw, are an important consideration with bone screws, particularly at small major diameter sizes thereof, e.g. 7.5 mm and less. Most failures of bone screws during insertion occur at the smaller screw sizes. More particularly, as the surgeon applies torque to the screw via a cannulated driver tool, the torsional forces can cause the screw to shear leaving only a lower portion that is partially driven into the bone material with the upper portion broken off from the remainder of the screw. At this point, additional medical intervention is necessary to remove or otherwise deal with the partially implanted screw portion and any broken off portions that may be loose at or around the implant site. Generally, with small screw sizes increasing the strength of the screws comes at the expense of having a larger cannula.

Similarly, the pull-out resistance of small screws can be compromised with increasing strength. The pull-out resistance is typically dependant on the purchase of the screw or its thread depth. With stronger, thicker-walled screws, the depth of the threads cannot be maximized for a particular size screw. In other words, if the screw cannula size is kept constant and the thread major diameter is not changed, the screw purchase will increase only with a generally corresponding decrease in screw strength.

Accordingly, there is a need for a cannulated bone screw particularly in small sizes thereof that allows it to be used with larger and firmer guide wires during implantation thereof. More particularly, small sizes of screws are needed that have an optimal combination of screw strength, cannula size, and thread purchase.

SUMMARY OF THE INVENTION

In accordance with the present invention, small cannulated bone screws are provided that are optimized in terms of their bending and torsional strength while still allowing for their implantation using relatively large diameter guide wires. To this end, the screws have a cannula that is maximized in size without a significant performance-related sacrifice such as in their strength characteristics. Also, the thread purchase of the small screws herein can be maximized so that the screws also have good pull-out resistance, as described further hereinafter.

More particularly, the bone screws at the smallest major diameter sizes, e.g., 3.0 mm-4.5 mm (which can be slightly oversized at 0.185 inch), include an optimum combination of strength and cannula size, without significantly sacrificing their pull-out resistance. For those small bone screws that are slightly larger, e.g. 5.5 mm-7.5 mm, the combination of their strength and pull-out resistance is optimized, without requiring a significant sacrifice in the size of their cannula. At these larger sizes, the size of the guide wire is typically not as much of a problem as with the smallest sizes.

Accordingly in one aspect, the present high strength small bone screws can be divided into the smallest screws where after strength, the following features are optimized as listed in order of importance: (1) cannula size, and (2) thread purchase. With small bone screws having a larger size, these features are reversed in their order of importance from an optimization standpoint as: (1) thread purchase, and (2) cannula size, which reflects the identification of guide wire size as being more important for the smallest screws versus those that have a slightly larger size such as in the 5.5 mm-7.5 mm range.

In another aspect, the invention relates to a set of small bone screws ranging in major diameter size from 3.0 mm up to 7.5 mm as by 0.5 mm increments, where the set is provided with an optimized combination of performance related characteristics including strength, cannula size, and thread purchase. As the entire screw set is optimized, a user need not seek out individual sizes of screws in the small screw range as set out above from different suppliers to achieve the high performance levels, as may be desired from these bone screws. Instead, the screw set herein can be obtained to achieve the high performance desired with any screw in this range of small sized screws. This range can be, more specifically, between 3.0 mm and 4.5 mm with their features optimized as discussed earlier.

As previously described, screw breakage during implantation is a problem particularly at the small sizes for bone screws that the present invention addresses. With the high strength provided to the present bone screws, and particularly to the annular wall extending along the shank thereof, it has been found that with excessive applied torque to the screw at the screw head driving surfaces, as when bone material becomes harder or increasingly difficult to penetrate with the preferred self-tapping screws herein, rather than shearing of the screw shank, the screw is stripped as by deformation of the driving surfaces. In this manner, the present screws do not break into distinct portions as often occurs with prior small bone screws before stripping. Thus, there is not the problem of having to locate the broken off portion or pieces of screws at or around the implantation site during a surgical operation employing the small bone screws herein, and removal of the whole of the stripped screws is also easier.

Moreover, the present high strength small bone screws allow for shallower drive surfaces to be employed in the screw head. With greater screw strength, the drive surfaces can be made more resistant to stripping by decreasing their surface area as by making them shallower vis-a-vis standard depths for driving surfaces for a particularly sized screw head, while still allowing surgeons to apply sufficient levels of torque to the screw for driving it into the bone material. The strength of the screw wall is sufficiently high so that it is still greater than the resistance to stripping of the reduced depth driving surfaces so that stripping occurs prior to screw breakage at excessive applied torque levels. Accordingly, the present high strength small bone screws can have drive surfaces that are optimized in terms of their resistance to stripping and still having stripping occur at excessive torque levels and in any event prior to screw breakage along the shank wall thereof.

DETAILED DESCRIPTION OF THE PREFERRED EMBODIMENTS

Figure 3A:
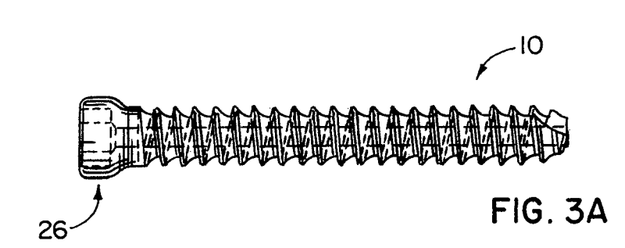
FIGS. 3A and 3B are directed to the cannulated bone screw of the present invention showing a different head and shank configuration including threads along the full shank length.

In FIGS. 1A-1D, a screw apparatus 10 in the form of bone screw 10a for being implanted into bone material is shown having one preferred configuration thereof. The bone screw apparatus 10 has an elongate shank 12 having proximal and distal ends 14 and 16, respectively. The shank 12 has external threads 18 formed along the shank 12 between the ends 14 and 16 thereof. As shown in the screw 10 of FIG. 1A, the screw shank 12 is only partially threaded from the distal self-tapping and self-drilling end 16 to approximately midway along the length of the shank 12 leaving an unthreaded section 20 thereof. Alternatively, the entire length of the shank 12 less screw head 26 can be threaded, as shown in FIG. 3A.

Figure 1A:
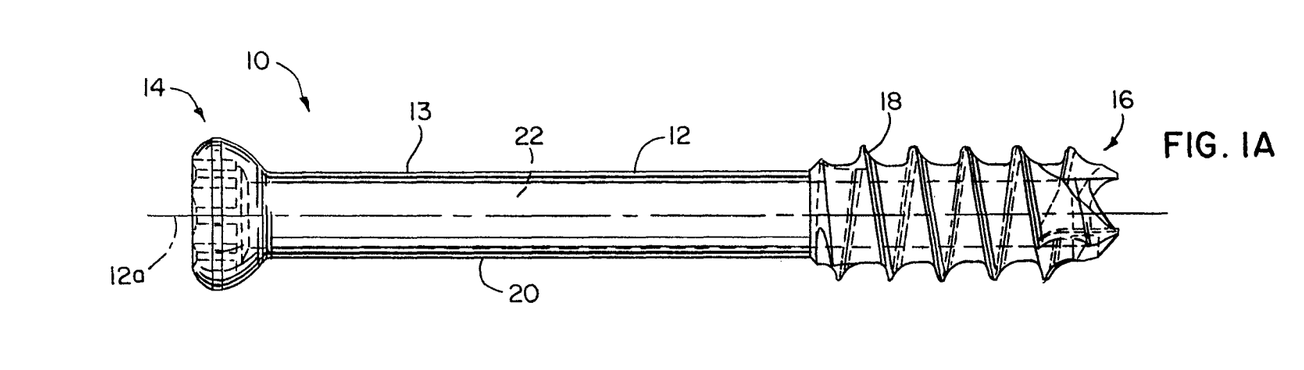
FIGS. 1A-1D are various views of a cannulated bone screw in accordance with the present invention showing a screw head having hex configured driving surfaces and a partially threaded elongate shank.
Figure 1B:
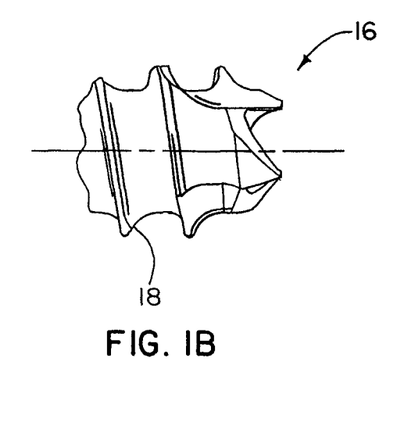
Figures 1C, 1D:
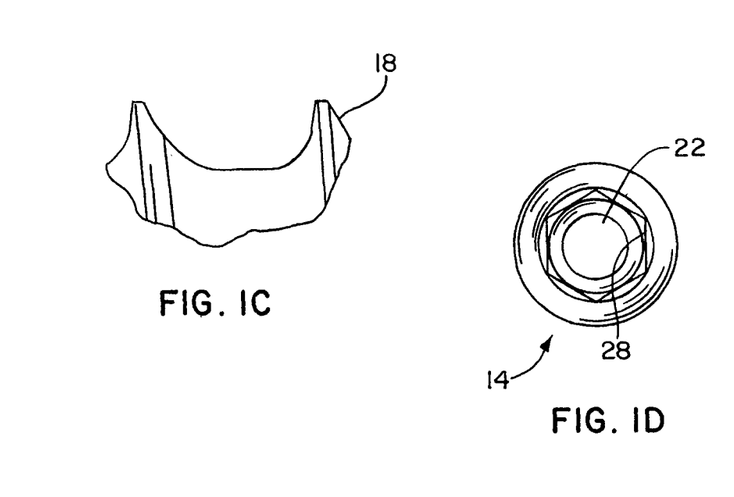
Figure 4:
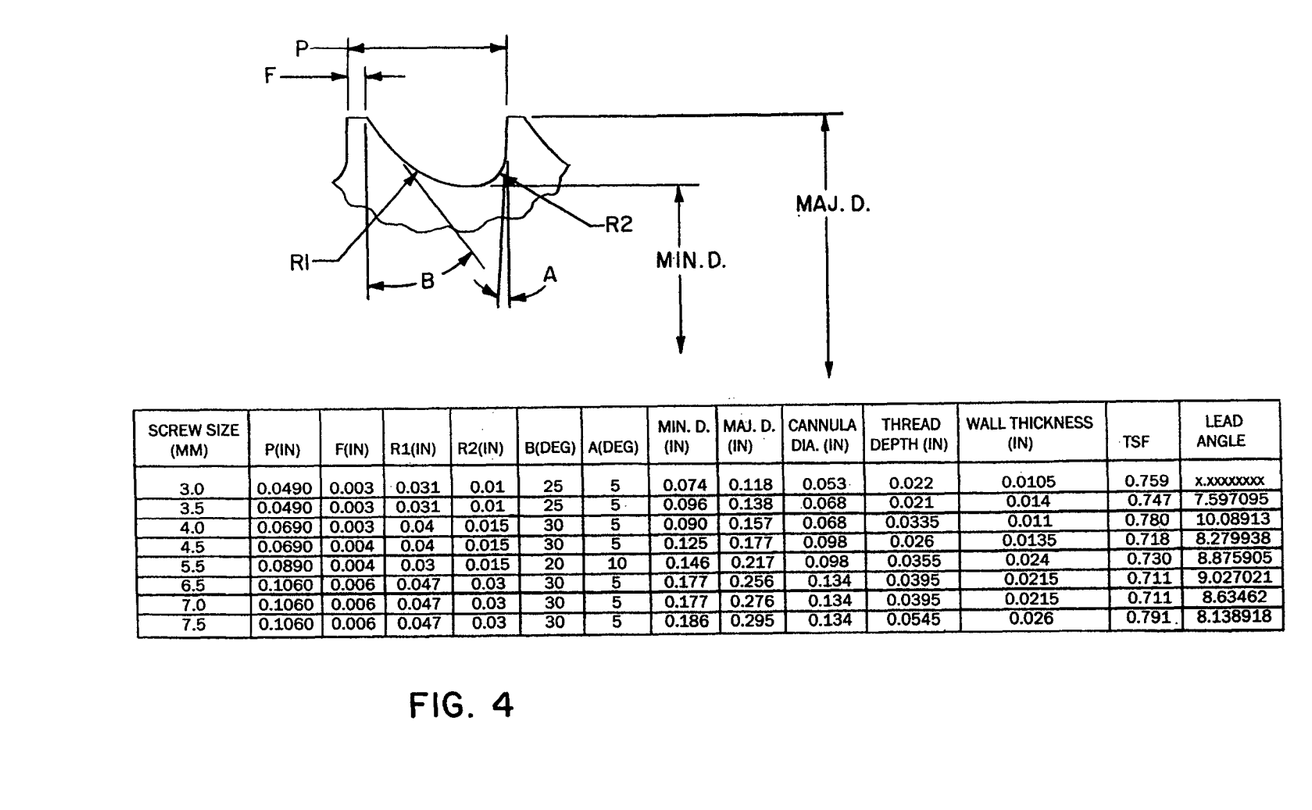
FIG. 4 is a schematic and a chart showing dimensions of the present bone screws as indicated on the schematic.

Referring to FIG. 4 and taking measurements for one of the listed screws 10, the thread outer or major diameter can be approximately 0.138 inches or 3.5 millimeters. As can be seen in FIGS. 1A and 1D, the shank 12 has a generally annular wall 13 including a throughbore or cannula 22 that extends the full way through the shank 12 from the proximal end 14 to the distal end 16 thereof. With the 3.5 millimeter major diameter on the threads 18, the screw 10a herein is formed with a relatively large cannula 22 having a diameter of 0.068 inches or 1.73 millimeters. With a wall thickness as measured between the minor diameter of 0.096 inch and the cannula diameter 0.068 inch of approximately 0.014 inch, for the given thread outer diameter, the cannula bore diameter of 0.068 inches is significantly improved over prior similar small screws having like dimensions for their corresponding thread major diameter. The bending and torsional strength of the screws 10a is kept high and comparable to similarly sized prior screws, as will be discussed further hereinafter. The screw 10 has a maximum bending moment indicative of its bending strength of 13.002 in/lbs, and a maximum shear moment indicative of its torsinal strength or shear resistance of 12.999 in/lbs. Further, the thread depth of 0.021 inch and thus purchase of the 3.5 mm screw 10 is still approximately the same or slightly better than prior comparable screws.

Figure 6:
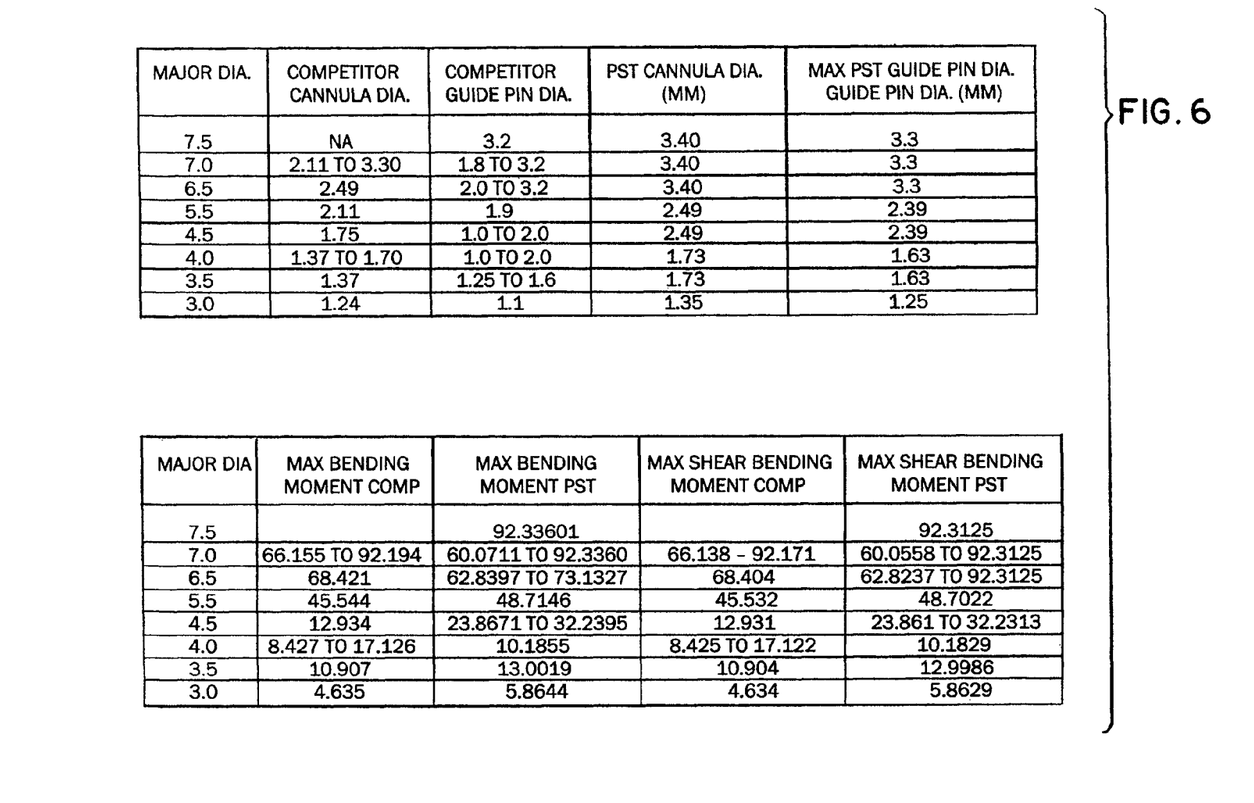
FIG. 6 is a chart showing bending and shear strength measurements for the present bone screws compared to prior bone screws.
Figure 7:
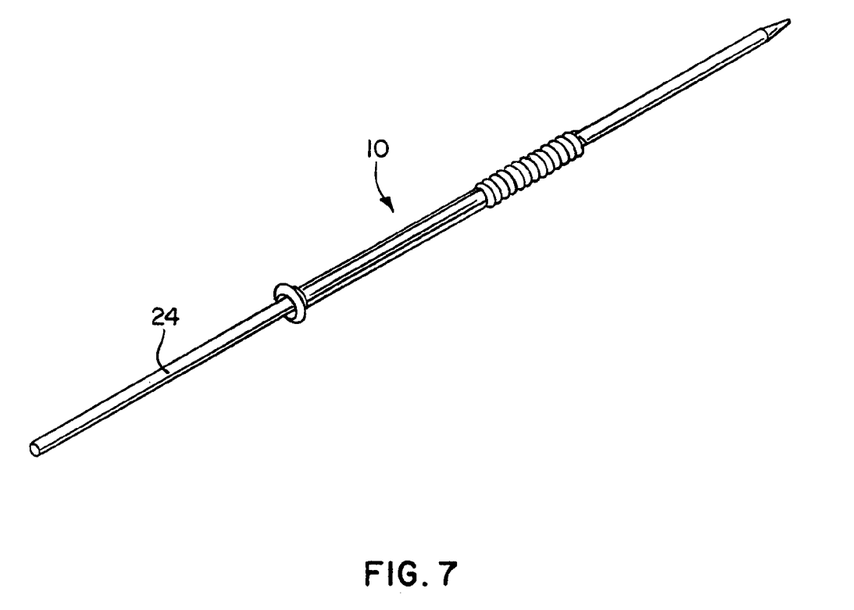
FIG. 7 is a perspective view of a small bone screw in accordance with the present invention having a relatively large diameter guide wire extending through the cannula thereof.

As can be seen in the chart of FIG. 6, the cannula 22 of the 3 mm screw 10, for instance, is increased by approximately eight percent over those provided in prior similar small screws. Likewise, the larger cannula allows for a larger guide wire 24 (FIG. 7) to be utilized with the small screw 10 herein. In this regard, the guide wire 24 can likewise be increased in size by a similar percentage over guide wires used with prior small screws, assuming a 0.1 mm clearance provided between the outer diameter of the guide wire 24 and the diameter of the cannula bore 22. It has been found that for the smallest screw sizes herein in the range of 3.0 mm to 4.5 mm, the cannula size has been maximized without a corresponding sacrifice in strength. In this manner, the present screws 10 of the smallest sizes herein can have the combination of the small size vis-a-vis their outer diameter, generally 4.5 millimeters and lower, while still obtaining the benefit of stiff guide wires 24 for use therewith by way of the relatively large diameter cannulas 22 formed therethrough. On the other hand, with the screws 10 at the larger end of the spectrum of small sizes, 5.5 mm-7.5 mm, where guide wire size is not as important, these larger screws 10 are provided with thread purchase that is optimized usually via a thinning of the screw wall 13 in comparison to prior screws while still maintaining the strength characteristics of the screws so that they are comparable to or exceed those of similarly sized prior screws. Even in these larger screw sizes, the diameter of their cannulas 22 will generally meet or exceed those of prior screws of similar sizes despite the greater emphasis placed on thread purchase at these sizes.

Figure 5:
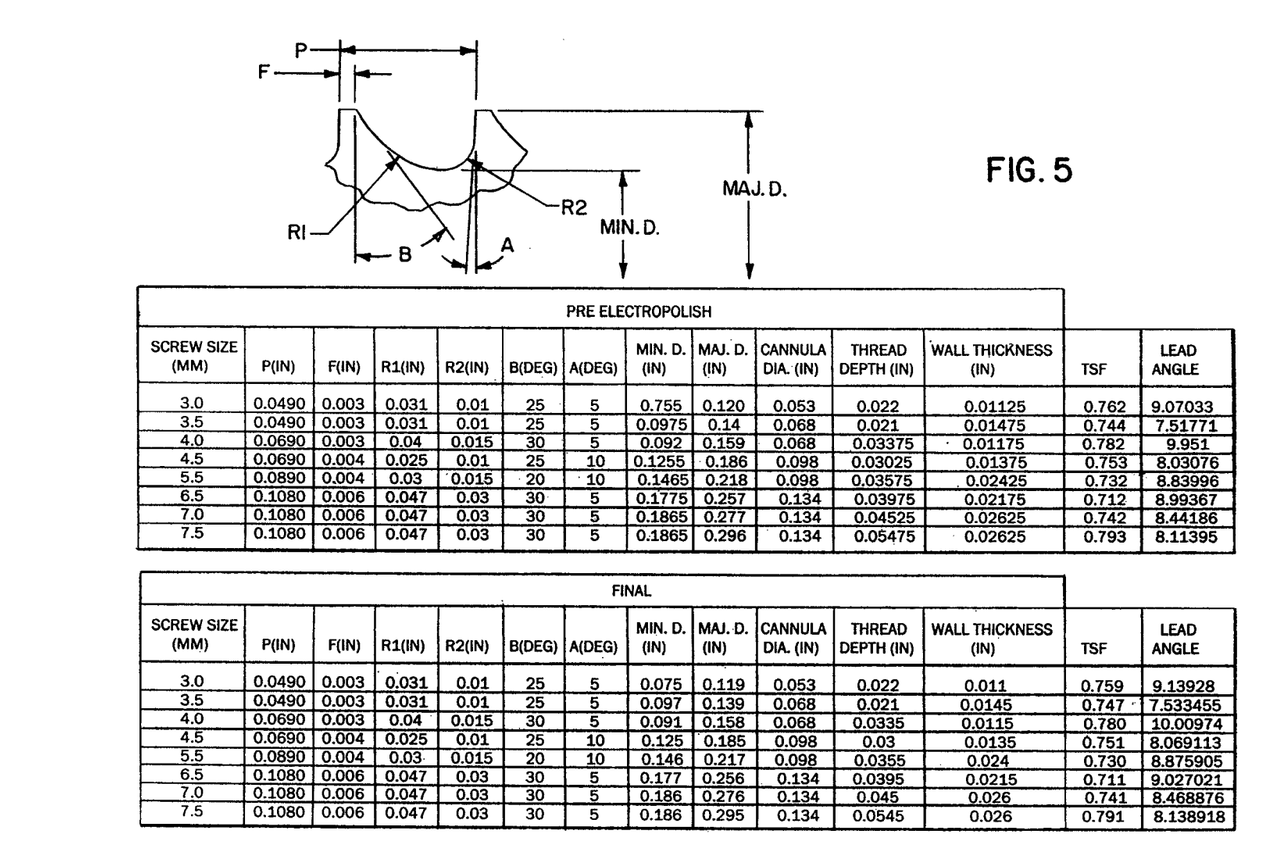
FIG. 5 is a chart similar to FIG. 4 showing more preferred dimensions for the present bone screws both pre-electropolishing and after electropolishing.

Referring to the charts of FIGS. 4-6, it can be seen that similar results are obtained for the bone screws 10 herein having thread diameters ranging from 3.0 millimeters up to 7.5 millimeters in terms of having larger cannula bores 22 therefor relative to prior cannulated screws. At the same time, the present screws 10 do not sacrifice performance and strength characteristics thereof relative to similarly sized prior screws which have smaller cannulas and/or worse performance and strength characteristics. In one respect, the threads 18 of the screws 10 herein can still be configured so that they are maximized in terms of holding power or purchase they provide in either cancellous bone material or in the cortex where less aggressive threads, i.e. smaller thread depth, can be employed. Particularly in cancellous material, the thread depth can be maximized while at the same time keeping the diameter of the cannula bore 22 to a maximum for fitting relatively large guide wires 24 therethrough. As mentioned, this is particularly true in the higher sizes for the present small bone screws 10 between 5.5 mm and 7.5 mm in their major diameters.

Figure 2A:
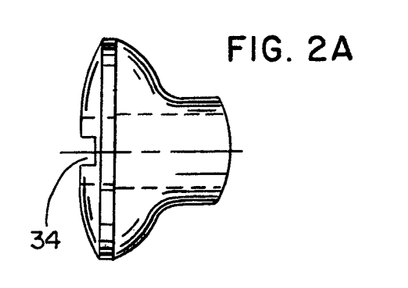
FIGS. 2A-2C are views of an alternative screw head having driving surfaces formed in a cruciform configuration.
Figure 2B:
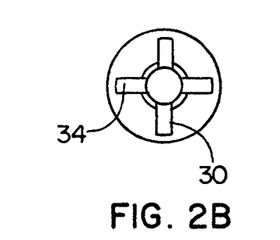
Figure 3B:
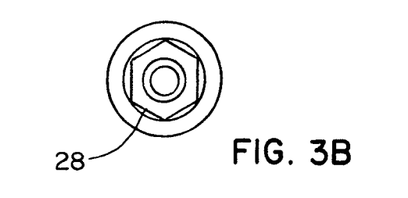

The screw 10 is provided with an enlarged head 26 at its proximal end 14 having an internal driving surface such as hex surfaces 28 (FIGS. 1D and 3B) for turning of the screw shank 12 about its axis 12a and sinking it into the bone material via an appropriately configured hex cannulated driver. Alternatively, the enlarged head can be provided with a cruciform or cross-slotted driving surfaces 30, as best seen in FIG. 2B. One significant concern with small screws such as the screws 10 herein is that the applied torque or torsional forces via the driver to start threading the screws 10 into the hard bone material can cause shearing of the screw shank 12 such as at the head 26 thereof where the torque is being applied. In this regard, the present screws 10 are provided with predetermined levels of bending and torsional strength that meet or exceed those provided by similarly sized prior screws even where the prior screws have smaller cannulas and thus thicker shank walls than the present screws 10, as illustrated in the empirically derived screw strength numbers in the chart of FIG. 6.

For this purpose, the cannulated screws 10 herein are preferably formed from a predetermined high strength material. One such material that has been found useful for forming the screw 10 with the desired combination of strength, thread size for pull-out resistance and cannula size for allowing the present small screws 10 to be accurately guided by larger guide wires 24 is an austenitic stainless-steel alloy essentially nickle-free, e.g. a weight percentage of nickle of 0.010 maximum, and having a high nitrogen content, e.g. greater than 0.90 weight percentage. The BioDur® alloys provided by Carpenter Specialty Alloys of San Diego, Calif., have been found to be suitable for the above-specified purpose. To this end, the high strength of the preferred screw material herein allows the present screws to be more precisely constructed in terms of their cannula size and thread depth while still meeting the strength requirements for bone screws that are of the small sizes as presently described so as to more readily avoid over design in this area. Accordingly, the present screws 10 are provided with performance enhancements while allowing the strength with which they are formed to be carefully controlled to avoid screw breakage problems.

Figure 2C:
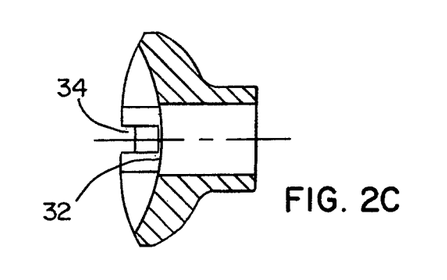

More particularly, the strength of screw walls 13 are sufficiently high that even with excessive applied torque at the driving surfaces 28 or 30, the screws 10 will not break as by shearing of their screw walls 13 and instead the high torques forces will first cause a stripping deformation of the drive surfaces 28 or 30. Referring to FIGS. 2A-2C, the head 26 can be provided with a central recess 32 that opens upwardly and has notches 34 extending radially therefrom. Four equally spaced, i.e. by 90 degrees, notches 34 can be provided to form the cross-slot or cruciform configuration for the driving surfaces 30.

The notches 34 are raised relative to the central recess 32 so that they are shallower than the recess at the radially inner interface therewith. In other words, the recess 32 has a greater depth at its center than do the radial notches 34. By way of example for the 3.0 mm screw, the head 26 can have an axial length of approximately 0.055 inch, with the notches 34 recessed to an axial depth of 0.015 inch. The central recess 32 can have a maximum axial depth at its center of approximately 0.030 inch. With the 3.0 mm screw including sizes as shown in the charts of FIGS. 4 and 5 and having its screw head 26 configured as described above, excessive-applied torque at the driving surfaces 30 will cause them to deform prior to breakage of the screw wall 13 due to the high strength thereof. It is believed that with the high strength screws 10 herein, the notches 34 including the drive surfaces 30 thereof can be further reduced in depth relative to the screw head size to better resist deformation thereof. This reduced depth driving surface 28 or 30 is sized so that a surgeon can still apply sufficient torque thereto via a cannulated driving tool for driving the screw 10 into bone material. Even with greater deformation resistance, the screw wall 13 has sufficient strength so that the reduced depth driving surfaces 28 or 30 will first deform prior to a shearing of the screw wall 13.

As is apparent, the present screws 10 are provided in a wide variety of sizes including shanks 12 that are partially threaded (FIG. 1A) and those that are fully threaded (FIG. 3A) and having heads 26 with either hex or cruciform driving surfaces 28 and 30, respectively. Each screw size based on screw major diameters can be provided with different screws at that size based on the end-to-end length of the shank 12 and the distance along the shank 12 from the distal end 16 that is threaded. Nevertheless, through the full range of the set of screws 10, they are provided with a better or optimized combination of torsional and bending resistance strength, large cannula diameter and thread depth, with the last two features having an order of priority that depend on whether the screws 10 are toward the lower or upper ends of the range of screw sizes herein as previously described. In those instances where the prior screws have similar major diameters along with similar cannula sizes, it is believed that the present screws 10 will be improved in strength, especially from a torsional strength standpoint. In this regard, there are no prior systems that provide the full range of small screw sizes ranging from 3.0 millimeters to 7.5 millimeters with the corresponding large cannula sizes and/or thread depth as set forth herein. In particular, applicant's screws 10 are significantly improved in the smallest sizes of the screws from 3.0 millimeters to 4.5 millimeters where almost none of the prior screws are able to approach the large cannula sizes achieved herein along with the strength provided for the present smallest screws.

Ultimately, one screw performance ratio can be defined as being determined by dividing the thread major diameter by the cannula diameter which is minimized for the full range of the present screws 10, and in particular for the smallest screw sizes, 3.0 mm to 4.5 mm. Where there are prior individual screws that meet this ratio, the prior screws will not be able to meet the strength characteristics of the present screws in particular with respect to the torsional and bending strength that the corresponding size screw 10 achieves or, especially at the larger screw sizes, 5.5 mm to 7.5 mm, the pull-out strength or resistance of the prior screw will be compromised by having less thread depth. Accordingly, another screw performance ratio can be defined as being determined by dividing the thread major diameter by the thread depth, which again is minimized for the present screws, and in particular for those that are toward the higher end in the range of small size screws 10 herein, 5.5 mm to 7.5 mm. Thus, each of the small sizes of screws 10 herein is able to exceed cannula sizes provided by prior screws and/or provide an enhanced or optimized combination of cannula size for improved screw implantation, thread purchase for providing high pull-out force resistance, and bending and/or torsional strength to allow the screw to resist shearing when being torqued for being rotatably driven into hard bone material. There are no prior small screws that have the above features, nor do they contemplate the same except in larger screw sizes where there is more room, i.e., screw material, for implementation of these optimized features and where such features may not be as critical, e.g. cannula size.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

We claim:
1. A bone screw apparatus comprising:
 a small bone screw having an elongate shank of a predetermined high strength alloy material and including proximal and distal ends thereof;
 external threads along the shank having a predetermined outer diameter, wherein the predetermined outer diameter is in a range of approximately 6.5 mm at a minimum diameter thereof up to a maximum diameter of approximately 7.5 mm;
 a predetermined inner diameter of the threads having a range of sizes between a minimum and a maximum thereof with thread depths defined between the outer and inner diameters of the threads;

a generally annular wall of the shank having a predetermined wall thickness;

an axial throughbore of the shank having a predetermined diameter of 3.4 mm; and a first predetermined screw performance ratio defined by dividing the inner diameter of the threads by the diameter of the axial throughbore in the shank, the first ratio being less than approximately 1.5, to maximize the size of the axial throughbore to permit a relatively large and stiff guide wire to be inserted therethrough.

2. The bone screw apparatus of claim 1 wherein the bone screw has a second predetermined screw performance ratio defined by dividing the throughbore diameter by the predetermined wall thickness, the second ratio being greater than approximately 4.0.

3. The bone screw apparatus of claim 1 wherein the bone screw has a third predetermined screw performance ratio defined by dividing the outer diameter of the threads by the predetermined wall thickness, the third ratio being greater than approximately 6.0.

4. The bone screw apparatus of claim 1 wherein the predetermined wall thickness is minimized by the first predetermined screw performance ratio for providing the maximized diameter of the axial throughbore, and the annular wall has a predetermined high torsional strength of between approximately 62.82 in/lbs at the thread outer diameter of approximately 6.5 mm and 92.31 in/lbs at the thread outer diameter of approximately 7.5 mm.

5. The bone screw apparatus of claim 1 wherein the predetermined wall thickness is between approximately 0.546 mm at the thread outer diameter of approximately 6.5 mm and approximately 0.660 mm at the maximum thread outer diameter of approximately 7.5 mm.

6. The bone screw apparatus of claim 1 in combination with the guide wire, wherein the guide wire has a predetermined diameter of approximately 3.3 mm.

7. The bone screw apparatus of claim 1 wherein the predetermined alloy material comprises an essentially nickel-free austenitic stainless steel alloy including a high nitrogen content.

8. The bone screw apparatus of claim 1 wherein the screw has a head at one end thereof that includes driving surfaces recessed into the head, and the head is formed of the predetermined alloy material so that stripping deformation of the driving surfaces occurs prior to screw shearing along the shank including the head with high applied torque via a driver for the screws.

9. The bone screw apparatus of claim 8 wherein the screw head driving surfaces are recessed to a predetermined depth that is kept to a maximum with the high strength screw material allowing applied torque via the driver engaged with drive surfaces to rotatively drive the screw into bone material.

10. A bone screw apparatus, the bone screw apparatus comprising:

a small bone screw having an elongate shank;

external threads along the shank having a predetermined major diameter and a predetermined thread depth, wherein the predetermined major diameter is in a range of approximately 6.5 mm at a minimum diameter thereof up to a maximum diameter of approximately 7.5 mm;

an axial throughbore of the shank having a predetermined diameter sized for receipt of a guide wire therethrough, wherein the predetermined throughbore diameter is at least 3.4 mm;

a generally annular wall of the shank having a predetermined wall thickness, the annular wall being formed of a predetermined metal alloy; and a first predetermined screw performance ratio for the screw defined by dividing the predetermined throughbore diameter by the predetermined wall thickness, the first ratio being greater than approximately 4.0.

11. The bone screw apparatus of claim 10 wherein the bone screw has a second predetermined screw performance ratio defined by dividing the predetermined major diameter by the predetermined wall thickness, the second ratio being greater than approximately 6.0.

12. The bone screw apparatus of claim 10 wherein the predetermined diameter of the throughbore is approximately 3.40 mm.

13. The bone screw apparatus of claim 10 in combination with the guide wire, wherein the guide wire has a predetermined diameter of approximately 3.3 mm.

14. The bone screw apparatus of claim 10 wherein the predetermined thread depth is between approximately 1.00 mm at the thread major diameter of approximately 6.5 mm and approximately 1.384 mm at the maximum thread major diameter of approximately 7.5 mm.

15. The bone screw apparatus of claim 10 wherein the bone screw has a predetermined torsional strength between approximately 62.82 in/lbs at the thread major diameter of approximately 6.5 mm to approximately 92.3 in/lbs at the maximum thread major diameter of approximately 7.5 mm.

16. The bone screw apparatus of claim 10 wherein the metal alloy comprises an essentially nickel-free austenitic stainless steel alloy including a high nitrogen content.

17. The bone screw apparatus of claim 10 wherein the bone screw includes a head at one end thereof including recessed drive surfaces configured such that application of excessive torque levels thereto causes deformation of the drive surfaces prior to breakage of the screw walls.

18. A screw for use in implantation comprising:

a screw having an elongate shank of a predetermined metal alloy material, including an enlarged head at one end thereof;

a plurality of threads along the shank;

a major diameter of the threads, the major diameter being in a range of approximately 6.5 mm at a minimum diameter thereof up to a maximum diameter of approximately 7.5 mm;

a minor diameter of the threads having a size of approximately 4.8 mm or less;

a thread depth defined between the major and minor diameters of the threads;

an axial throughbore having a diameter sized to receive a guide wire therethrough for stabilizing the screw during implantation, the throughbore diameter being at least 3.4 mm;

a wall thickness of the screw shank having a predetermined size between the minor diameter of the screw and the throughbore diameter; and a first predetermined screw performance ratio for the screw defined by dividing the major diameter by the wall thickness, the first ratio being greater than approximately 9.0.

19. The screw of claim 18 wherein the screw has a second predetermined screw performance ratio defined by dividing the thread depth by the wall thickness, the second ratio being greater than approximately 1.3.

20. The screw of claim 18 wherein the screw has a third predetermined screw performance ratio defined by dividing the diameter of the axial throughbore by the thread depth, the third ratio being greater than approximately 2.0.

21. The screw of claim 18 wherein the metal alloy comprises an essentially nickel-free austenitic stainless steel alloy including a high nitrogen content.

22. The screw of claim 18 wherein the predetermined wall thickness is minimized for providing the maximized diameter of the throughbore, and the screw wall has a predetermined torsional strength of between approximately 62.82 in/lbs at the thread major diameter of approximately 6.5 mm to approximately 92.31 in/lbs at the maximum major diameter of approximately 7.5 mm.

23. The bone screw apparatus of claim 18 wherein the screw head includes driving surfaces recessed into the head so that stripping deformation of the driving surfaces occurs prior to screw shearing along the shank including the head with high applied torque via a driver for the screws.

* * * * *